United States Patent [19]
Gianturco

[11] Patent Number: 5,258,000
[45] Date of Patent: Nov. 2, 1993

[54] TISSUE APERTURE REPAIR DEVICE

[75] Inventor: Cesare Gianturco, Champaign, Ill.

[73] Assignee: Cook Incorporated, Bloomington, Ind.

[21] Appl. No.: 797,321

[22] Filed: Nov. 25, 1991

[51] Int. Cl.$^5$ .............................................. A61B 17/00
[52] U.S. Cl. .................................. 606/151; 606/213; 606/215
[58] Field of Search ................ 606/213, 215, 151, 232

[56] References Cited

U.S. PATENT DOCUMENTS

| | | | |
|---|---|---|---|
| 3,124,136 | 3/1964 | Usher | 606/213 |
| 3,874,388 | 4/1975 | King et al. | 606/232 |
| 4,595,007 | 6/1986 | Mericle | 606/221 |
| 4,917,089 | 4/1990 | Sideris | 606/215 |
| 5,053,047 | 10/1991 | Yoon | 606/232 |
| 5,108,420 | 4/1992 | Marks | 606/151 |
| 5,122,155 | 6/1992 | Eberbach | 606/213 |

FOREIGN PATENT DOCUMENTS

| | | |
|---|---|---|
| 2822603 | 11/1979 | Fed. Rep. of Germany . |
| 9206639 | 4/1992 | World Int. Prop. O. . |

*Primary Examiner*—Stephen C. Pellegrino
*Assistant Examiner*—Jeffrey A. Schmidt
*Attorney, Agent, or Firm*—Richard J. Godlewski

[57] ABSTRACT

A tissue aperture repair device which is inserted using either an openly or minimally invasive surgical procedure for at least partially covering a tissue aperture or hernial ring. The repair device includes a foldable sheet of material that is maintained with support means in an unfolded shape. The support means includes a second sheet of material attached to the circumference of the foldable sheet for forming a cavity therebetween. An elastic stiffener wire is inserted into the cavity for maintaining the device in its unfolded shape. Percutaneous insertion of the device is accomplished with the inclusion of an introducer in which the device is folded about the distal end thereof and contained within a containment sheath. The device is percutaneously inserted into the abdominal cavity of a patient, unfolded, and extended to the unfolded shape with an elastic stiffener wire also percutaneously inserted through the introducer. The device is attached to tissue surrounding the hernial ring using suture material or helical coil fasteners. Alternatively, the device is fastened using an affixation suture extending from the foldable sheet of material.

25 Claims, 4 Drawing Sheets

TISSUE APERTURE REPAIR DEVICE

TECHNICAL FIELD

This invention relates generally to tissue aperture repair devices and, in particular, to an unfoldable tissue aperture repair device which is percutaneously insertable for at least partially covering a tissue aperture or opening, such as a hernial ring, and for promoting tissue growth thereon.

BACKGROUND OF THE INVENTION

As often occurs, a hernia is formed when the abdominal wall has a weak area that is not capable of keeping the peritoneum in place. When a hernia occurs, a bulge in the peritoneum, called a hernial sac, penetrates through an aperture or opening, called a hernial ring, in the abdominal wall. In corrective surgery, the hernial sac is passed back through and away from the hernial ring. To prevent the hernia from recurring, a barrier material is commonly positioned over the hernial ring and affixed to the surrounding tissue to block passage of the peritoneum therethrough and to strengthen or reinforce the abdominal wall about the hernial ring.

This strengthening or reinforcing is traditionally accomplished by stitching a piece of tissue across the hernial ring. With recent minimally invasive surgical procedures, hernial ring repair is percutaneously performed with the aid of an endoscope, or more particularly a laparoscope, and one or more trocar access sheaths inserted into the abdominal cavity, thereby avoiding a much more invasive procedure such as open surgery with accompanying trauma to surrounding tissue. Instruments and material are inserted through these trocar access sheaths for effecting the repair. During the minimally invasive laparoscopic procedure, two access sheaths are typically inserted through the peritoneum about the hernial ring to pull barrier material such as synthetic prosthetic mesh through one sheath and to spread the mesh over the hernial ring with a grasper inserted through the other sheath. Following positioning, the mesh is affixed to the abdominal wall with clips or suture material.

A problem with the use of prosthetic mesh is that considerable stress or tension is placed on the mesh since it prevents organs or tissue from protruding through the abdominal or thoracic wall. This tension pulls the sutures anchoring the mesh and causes trauma to the adjacent tissue. Furthermore, the tension may be unevenly distributed over the mesh and sutures. The sutures under severe stress may be torn from the adjacent tissue. Adjacent tissue that is torn or traumatized by stressed sutures impedes new tissue growth over the mesh. In some cases, the adjacent tissue damage enlarges the weak area or hernial ring, and subsequent surgery is required for performing additional repairs.

Another problem is the surgeon's difficulty in grasping and manipulating the mesh. With traditional open surgery, the surgeon has direct access to the weak area or hernial ring, and a piece of mesh is readily positionable thereover. However, once wetted by bodily fluids at the repair site, some meshes are awkward to manipulate. In minimally invasive laparoscopic procedures, a sheet of mesh is folded or rolled for introduction through one of the trocar access sheaths. Again, once wetted by bodily fluids at the repair site, the mesh is difficult to spread smoothly over the repair site.

The problem of positioning the prosthetic mesh in a smooth sheet over the repair site is compounded when the mesh is placed between layers of tissue. The mesh is placed between the transversalis and Poupart's ligament in the well-known subfascial technique for repairing a direct inguinal hernia with weak fascia, for example, and between the peritoneum and transversalis in the well-known two-layer technique for repairing large defects using mattress sutures about the periphery of both sheets of mesh. Furthermore, the mesh is difficult and awkward to smooth into place when sandwiched between these layers.

SUMMARY OF THE INVENTION

The foregoing problems are solved and a technical advance is achieved in either open surgery or minimally invasive laparoscopy with an illustrative foldable, tissue aperture repair device that is maintainable in an unfolded shape for at least partially covering the tissue aperture. The repair device comprises a foldable sheet of material having an unfolded shape and support means attached thereabout for maintaining the sheet in its unfolded shape.

The support means includes a stiffener such as an elastic metallic wire for applying force to the foldable sheet and maintaining the sheet in its unfolded shape. The support means further includes attachment means, such as a second sheet of material attached about the circumference of the foldable sheet of material, for attaching the stiffener to the foldable sheet. The second sheet of material attached about the circumference of the foldable sheet forms a cavity therebetween. The stiffener is inserted in the cavity through an opening therein. Alternatively, the elastic stiffener is directly attached to the foldable sheet utilizing attachment means such as suture material, biocompatible adhesive, clips, etc. The stiffener can also be woven through the foldable sheet about the circumference thereof.

The stiffener advantageously expands the foldable sheet and maintains it in its unfolded shape. The stiffener in the cavity expands the foldable sheet of material by conforming to the circumference of the foldable sheet to maintain the foldable sheet in an unfolded shape.

The tissue aperture repair device is advantageously used in both open surgery and minimally invasive laparoscopic procedures and further includes affixation means such as a helical fastener insertable through the foldable sheet or suture material extending from the sheet for affixing the foldable sheet of material in its unfolded shape to tissue positioned about the aperture.

In minimally invasive surgical procedures, the repair device advantageously includes an introducer attached to either the support means or the foldable sheet of material for applying the stiffener to the attachment means. In the illustrative embodiment, the introducer comprises a hollow tube positioned through an opening or collar to the cavity that is formed between the foldable and second sheets of material. The repair device further includes a sheath for containing and introducing the foldable and second sheets of material folded about the distal end of the introducer. The sheath and folded sheets of material contained therein are percutaneously introduced through a trocar sheath and into the insufflated peritoneal cavity. When introduced, the folded sheets of material and introducer are extended from the distal end of the containment sheath and into the body cavity. The stiffener is then inserted through the introducer and into the cavity between the foldable and second sheets of material to expand the foldable sheet to its unfolded shape.

The repair device further includes a wire guide for inserting the stiffener through the introducer and into the cavity between the foldable and second sheets of material. The wire guide advantageously includes a distal end that readily detaches from the proximal end of the stiffener when inserted into the device cavity. The stiffener advantageously comprises an elastic wire such as stainless steel or a superelastic wire of a nickel-titanium alloy such as nitinol for expanding and conforming to the shape of the device cavity and the outer circumference of the foldable sheet of material. The ends of the stiffener are shaped to prevent snagging or catching on the foldable and second sheets of material. The shape of the device cavity and the outer circumference are advantageously elliptical or circular in shape to present a smooth, evenly tensioned device surface for attachment to tissue about the aperture. The stiffener advantageously eliminates the problem of unwrapping and positioning wetted prosthetic mesh in both open surgery and minimally invasive endoscopic procedures.

After introduction into the peritoneal cavity during a minimally invasive procedure, the introducer of the device is detached from the unfolded sheets of material by engaging the collar or the material about the cavity opening against the distal end of the sheath while withdrawing the introducer therefrom. An affixation suture extending from the positioned, unfolded sheets of material is percutaneously drawn through the tissue aperture to fixedly position the device over the tissue aperture for subsequent tissue ingrowth. Affixation means such as helical coil fasteners or suture material are positioned through the unfolded material sheets to affix the repair device to tissue surrounding the hernial ring. The extending suture can be percutaneously affixed to the patient's skin for sole or additional device affixation or removed after positioning of the repair device and affixation to surrounding tissue with other affixation means. The foldable sheet of material positioned against the tissue aperture advantageously provides for the ingrowth of repair tissue.

DETAILED DESCRIPTION

Figure 1:
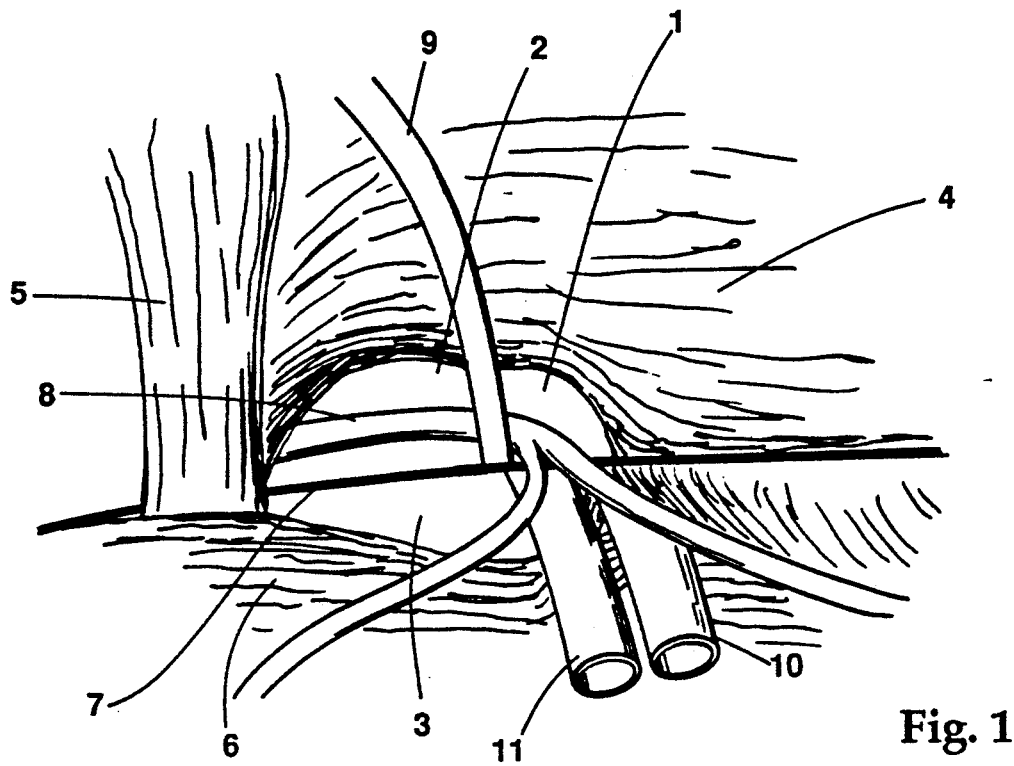
FIG. 1 depicts the inguinal canal viewed from the inside of the abdominal cavity.

Depicted in FIG. 1 is the inguinal canal in a male patient. The peritoneum and the transversal fascia have not been shown for the sake of clarity. Three potential tissue apertures, particularly hernial rings 1 and 2 for hernia inguinalis and ring 3 for hernia femoralis are indicated. Musculature 4 reflects the location of musculus obliquus internus and musculus transversalis, while musculature 5 reflects the location of musculus rectus. Hernial ring 3 is delimited by pubis and Cooper's ligament 6 and by inguinal ligament 7, which also delimits the two other tissue apertures or hernial rings. Spermatic cord 8 extends upwards through the inguinal canal past epigastric vessel 9 in Hasselbach's ligament and into the abdominal cavity. Femoral artery 10 and vein 11 are also shown.

Figure 2:
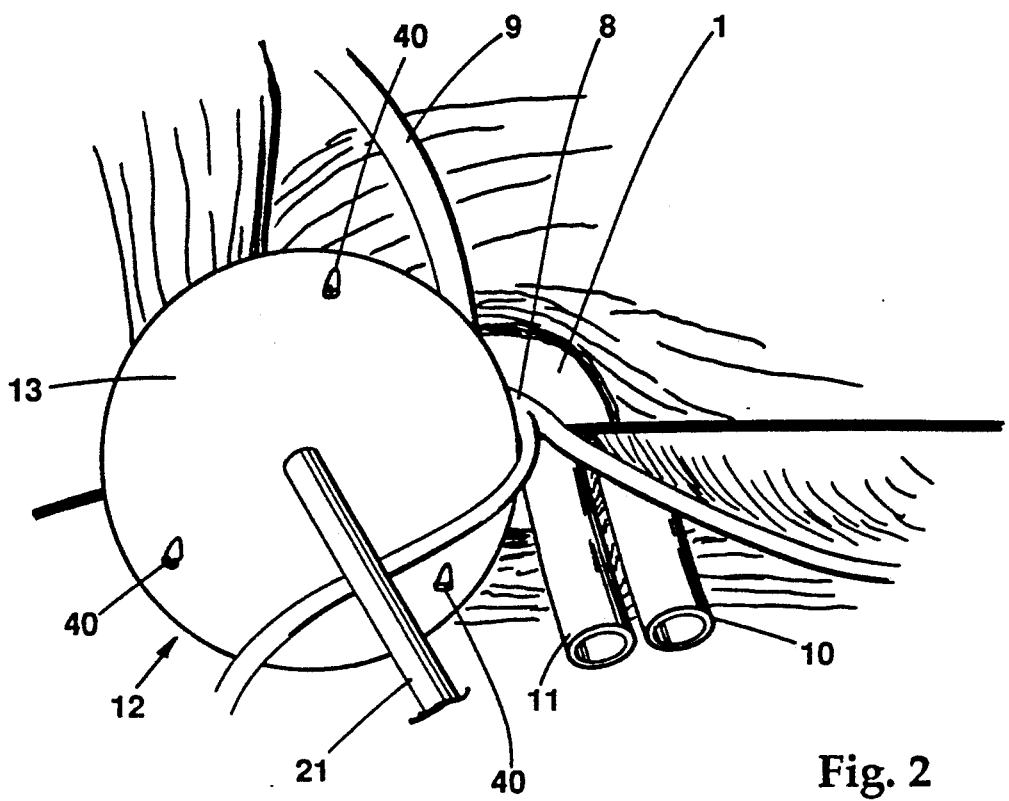
FIG. 2 is a corresponding illustration after the tissue aperture repair device according to the present invention has been positioned.

After a hernia is formed, the musculature around the inguinal canal is weakened, thereby increasing the risk of recurrent hernia. This may be eliminated by inserting, as depicted in FIG. 2, a tissue aperture repair device 12 across the major part of the tissue aperture or hernial ring, thereby preventing the peritoneum from penetrating through one of hernial rings 1-3. Device 12 has an unfolded elliptical or circular shape for abutting on part of the musculature of the abdominal cavity to strengthen it and for at least partially covering tissue apertures or hernial rings 1-3. As a result, spermatic cord 8, femoral artery 10 and vein 11 together with epigastric vessel 9 may concurrently pass freely by the tissue aperture repair device.

Figure 3:
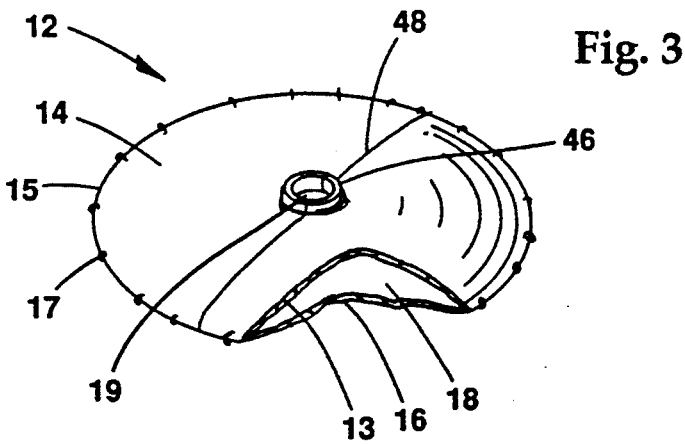
FIG. 3 depicts a partially sectioned pictorial view of an illustrative tissue aperture repair device of the present invention.

Depicted in FIG. 3 is a partially sectioned pictorial view of illustrative tissue aperture repair device 12 for at least partially covering a tissue aperture such as a hernial ring. The repair device includes foldable sheet 13 of material having unfolded circular shape 14 and circumference 15. When the repair device is used in open surgery, the material of the foldable sheet preferably comprises, for example, a porous prosthetic mesh material such as MARLEX material or other commercially available biocompatible materials for reinforcing or strengthening the tissue positioned about the tissue aperture or hernial ring and for providing a structure for tissue ingrowth about the aperture. MARLEX mesh material is a 6 mil monofilament knitted polypropylene material. The diameter of the unfolded circular shape is approximately 7 cm for at least partially covering the tissue aperture. Diameter sizes can vary preferably in the range from 5 to 10 cm. Preferably, only one tissue aperture repair device should be used to cover the tissue aperture or hernial ring. However, depending on the size and shape of the tissue aperture, several repair devices can be positioned over the aperture and overlapped for providing sufficient coverage of the aperture as desired by the attending physician. The unfolded shape of the sheet can also assume an elliptical shape for at least partially covering elongated tissue apertures or hernial rings. Centrally positioned opening 19 is formed in a single sheet of foldable material for inserting a stiffener therethrough as will be described hereinafter.

When the repair device is used in a minimally invasive laparoscopic procedure, the material of the foldable sheet preferably comprises, for example, a thin, DACRON or nylon, filtering or particulated material, which, for example, is commercially available from Tetco Incorporated, Briar Cliff Manor, N.Y., as their PE7-53/32 material. This thin, particulated sheet of material is easily folded or rolled tightly about an introducer for containment within a sheath and introduction through a trocar access sheath, which is commonly used in laparoscopic procedures. Foldable sheet 13 is formed from two sheets of the particulated material abutted and heat sealed to form centrally positioned and extending collar 46 with opening 19 therein, as depicted in FIG. 3. Seam 48 in foldable sheet 13 is formed by heat sealing the abutted ends of the two sheets of particulated material.

The tissue repair device also includes support means including a second sheet 16 of material attached about circumference 15 of foldable sheet 13 for maintaining the foldable sheet in unfolded circular shape 14. The foldable and second sheets 13 and 16 of material are attached about circumference 15 of the foldable sheet using a well-known heat seal process. When the repair device is used in open surgery and the integrity of the circumferential seal is a concern to the surgeon, suture material 17 is stitched about the circumference for added strength and support. Second sheet 16 of material also comprises a sheet of prosthetic mesh such as MARLEX material heat sealed to the foldable sheet of material about the circumference thereof. It is contemplated that a tightly woven or solid nonporous sheet of material such as silicone, GORTEX polymer material, polytetrafluoroethylene, or other commercially available biocompatible material can be used for preventing tissue ingrowth when positioned, for example, against the organs contained within the peritoneal or other internal cavity. This nonporous material may also be biodegradable. However, dog experiments have shown that preventing tissue ingrowth on the surface of the repair device facing internal organs is extremely difficult. A flap of the peritoneum positioned over the affixed repair device is preferred for preventing adhesions to internal organs. Virtual device cavity 18 is formed between foldable and second sheets 13 and 16 of material that are circumferentially attached together. The outer radial shape of device cavity 18 abuts circumference 15 and assumes unfolded circular shape 14 when a stiffener such as an elastic wire is inserted in the cavity.

The tissue aperture repair device also includes a stiffener for applying force to the foldable sheet of material to maintain it in an unfolded shape or condition. The length of the stiffener is selected to be longer than the circumference of the device to conform to unfolded circumference 15 when inserted in device cavity 18. The elastic stiffener wire may comprise a length of stainless steel wire approximately five times the length of the device circumference or a length of a nickel-titanium alloy wire such as commercially available nitinol preferably at least the length of the device circumference. When used as an open surgery repair device, both ends of the stiffener wire are bent into tight closed loops and soldered to prevent snagging. The ends of the wire are also curved to better conform the wire to the circumference of the cavity. When used in a minimally invasive procedure, the proximal end of the stiffener is attached to a wire guide for introduction into the device cavity.

Although device cavity 18 is illustrated as a flat circular disk when in the unfolded state, it is contemplated that the cavity may assume other shapes or configurations for receiving a stiffener for applying force to the foldable sheet of material for maintaining the foldable sheet in the unfolded shape. In particular, device cavity 18 can be formed as a circular ring with a length of narrow width material attached circumferentially about the foldable sheet of material. The internal edge of the narrow width material would be likewise attached about the circumference of the foldable sheet a short distance inward from circumference 15. The stiffener is then inserted into this circular ring device cavity for applying force for maintaining the foldable sheet in the unfolded shape. The stiffener in this instance could also be a straight length of elastic wire at least longer than the circumference of the device. Alternatively, the stiffener could also assume the shape of an elastic wire coil for providing even further flexibility for use in open surgery. It is also contemplated that a plurality of pockets of the second material could be diagonally attached to the foldable sheet and straight stiffeners be inserted therebetween for stretching the foldable sheet to the unfolded circular shape. When the second sheet of material does not completely cover the foldable sheet of material, the exposed side of the foldable sheet of material should inhibit tissue ingrowth. In such case, the foldable sheet can be multi-layered with one layer promoting tissue ingrowth and the other layer of the sheet inhibiting tissue ingrowth. Alternatively, the side of the foldable sheet anticipated for exposure to internal body organs may be coated with a well-known antifibrogenic coating for inhibiting tissue ingrowth and the formation of lesions.

Tissue aperture repair device 12 can be used in both open surgery and minimally invasive laparoscopic procedures. When used in open surgery, the stiffener is inserted through small diameter opening 19 into device cavity 18 during the manufacturing process. The device cavity is sealed, and the device is packaged for use by the physician. When the device is used in minimally invasive laparoscopic procedures, device cavity 18 communicates with opening 19 that is centrally positioned and extended by collar 46 in foldable sheet 13 of material for insertion of a percutaneous introducer therethrough. It is also contemplated that opening 19 can be formed in the second sheet of material. The introducer is inserted in opening 19 of the cavity to position the repair device against the tissue aperture.

Figure 4:
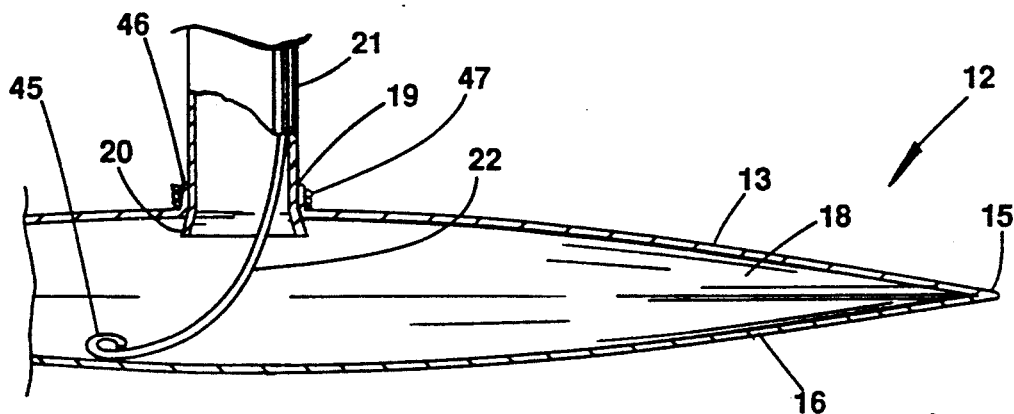
FIG. 4 depicts a partially sectioned side view of the tissue aperture repair device of FIG. 3 with a percutaneous introducer inserted therein.
Figure 5:
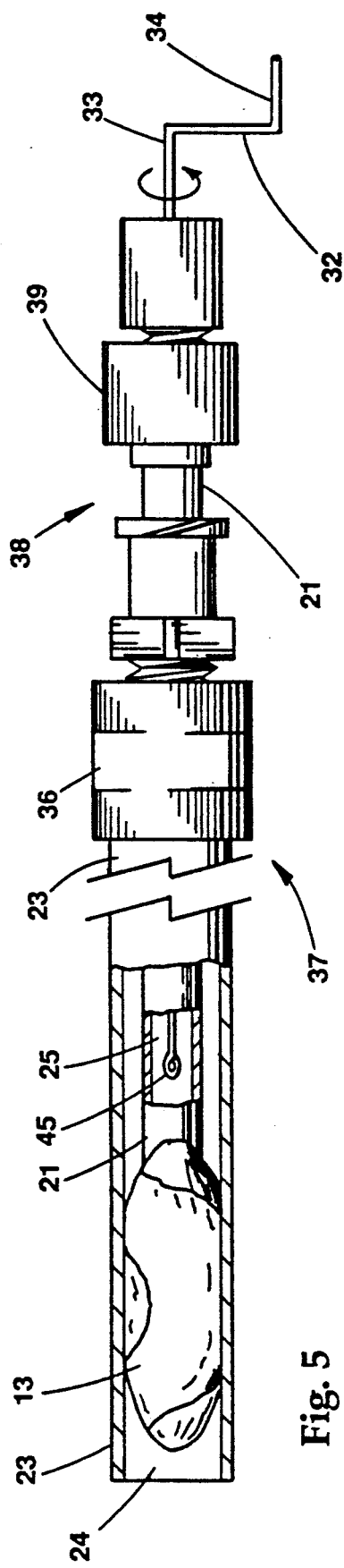
FIG. 5 depicts a partially sectioned view of the tissue aperture repair device of FIG. 4 in a folded condition and positioned in a containment sheath.

Depicted in FIG. 4 is a partially sectioned side view of tissue aperture repair device 12 with collar 46 and opening 19 centrally positioned in foldable sheet 13 and flared distal end 20 of percutaneous introducer 21 positioned therethrough. As previously described, device cavity 18 is formed between foldable and second sheets 13 and 16 of material bounded by the sheets and circumference 15 of the foldable sheet. Percutaneous introducer 21 includes hollow passageway 25 extending longitudinally therethrough for the insertion and passage of stiffener 22. The foldable and second sheets of material are folded together and wrapped around and about distal end 20 of the introducer and inserted into hollow longitudinal passageway 24 of containment sheath 23 as depicted in FIG. 5. The containment sheath with the tissue aperture repair device contained therein is inserted through a well-known trocar access sheath (not shown) which is introduced into the peritoneal cavity of the patient using a well-known surgical procedure.

Referring again to FIG. 4, when the folded tissue aperture repair device is extended from the distal end of containment sheath 23 into the peritoneal cavity of the patient, elastic stiffener wire 22 is passed through introducer 21 and into device cavity 18. By way of example, the elastic stiffener wire comprises approximately a 110 cm length of Series 302 or 304 stainless steel wire approximately 0.014" in diameter. The length of this wire is approximately five times the circumference (approximately 22 cm) of unfolded sheet 13 of material in unfolded shape 14. The distal end of the stiffener wire is rolled and soldered to form bead 45, which prevents the distal end of the wire from catching or snagging on the sheets of material. This length of elastic stiffener wire is passed through the percutaneous introducer and into device cavity 18, which expands and conforms to circumference 15 of foldable sheet 13 of material as depicted in FIG. 6.

Figure 6:
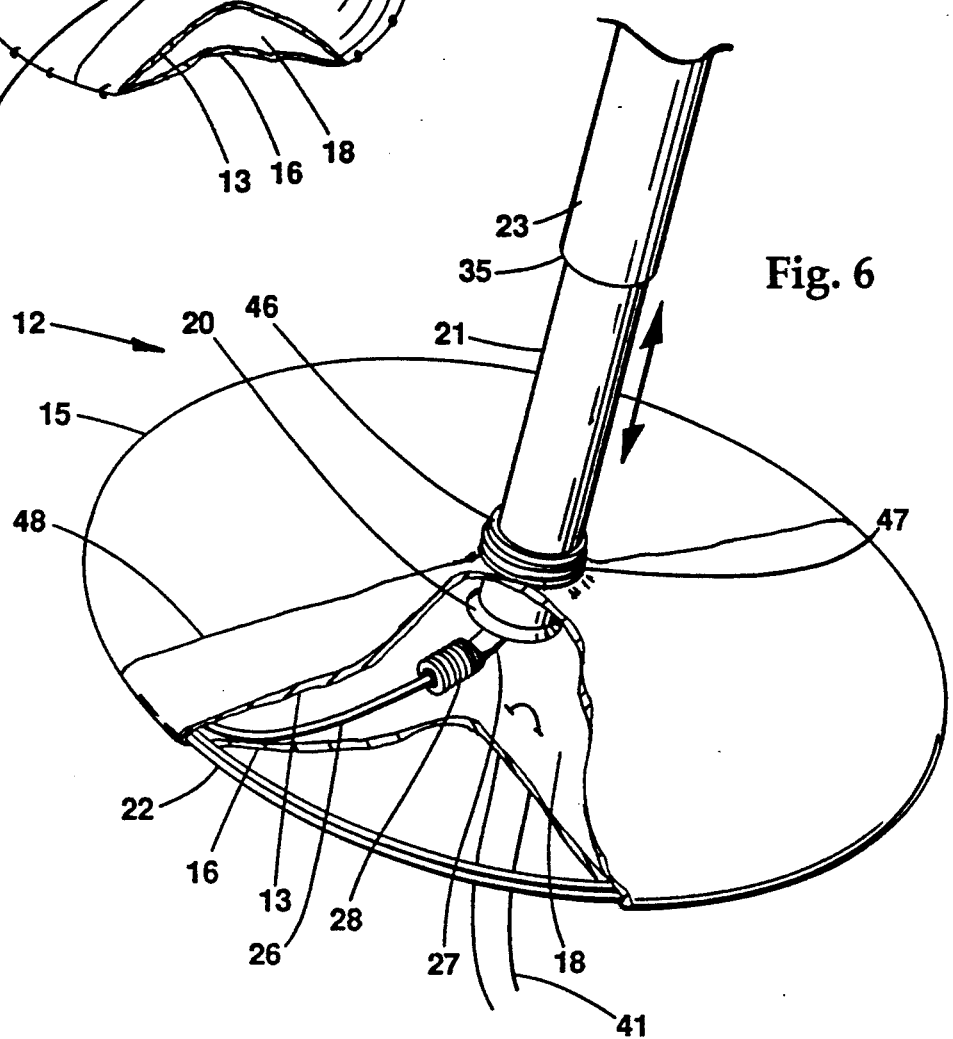
FIG. 6 depicts a partially sectioned view of the repair device of FIG. 4 in an unfolded shape and a stiffener being inserted therein for maintaining the device in the unfolded shape.
Figure 7:
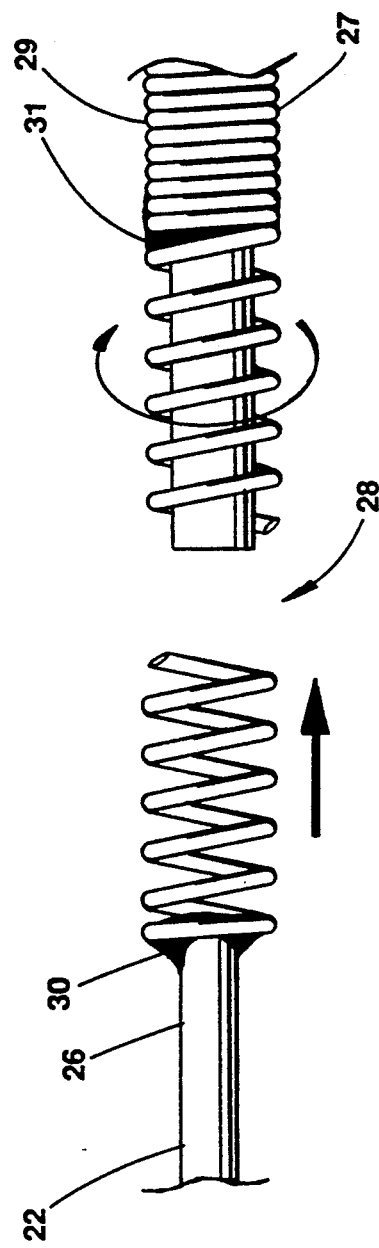
FIG. 7 depicts an enlarged view of the wire coil fastener of FIG. 6 interconnecting the proximal end of the stiffener and the distal end of the wire guide.

As depicted in FIG. 6, proximal end 26 of elastic stiffener wire is attached to wire guide 27 with detachable wire coil fastener 28. An enlarged view of wire coil fastener 28 attaching proximal end 26 of elastic stiffener wire 22 and distal end 29 of wire guide 27 is depicted in FIG. 7. The wire coil fastener comprises two segments of a 0.038" outside diameter coil of 0.008" stainless steel wire. One segment is attached to proximal end 26 of elastic stiffener wire 22, and the other segment is formed from the turns of wire guide 27. The wire guide segment of the wire coil fastener is formed by separating the coil turns of the wire guide about distal end 29 and fixedly positioning the separated turns using, for example, well-known silver solder bead 31. The segment of the wire coil fastener attached to proximal end 26 of the stiffener is affixed by silver solder bead 30 with the turns of the segment wound in the same direction. The wire guide and stiffener are interconnected by interleaving the turns of the wire coil fastener segments. By way of example, wire guide 27 has a 0.025" outside diameter and is commercially available from several medical device manufacturers such as Cook Incorporated, Bloomington, Indiana. The length of the wire guide is approximately 65 cm with proximal end 32 including two right angle corners 33 and 34 as depicted in FIG. 5 for rotating the wire guide in either a clockwise or counterclockwise direction. To detach elastic stiffener wire 22 from wire guide 27, proximal end 32 of the wire guide is rotated to disengage the interleaved segments of wire coil fastener 28 as depicted by the arrows in FIG. 7. When disengaged, the stiffener wire engages the circumference of device cavity 18.

By way of example, introducer 21 comprises a 50 cm length of polytetrafluoroethylene material tube having an thickness of approximately 0.015–0.020". As depicted in FIG. 4, distal end 20 of the introducer tube is flared in a well-known manner for retainage in device cavity 18. Typically, the distal end of the introducer tube is inserted through collar 46 and opening 19 of the foldable sheet of material and then flared in a well-known manner. Collar 46 is further affixed to the introducer tube with silk suture material 47 wound thereabout, tied, and glued with medical grade adhesive. Collar 46 and suture material 47 transversely position the unfolded and second sheets of material with respect to the introducer. The second sheet of material is then attached to the circumference of the foldable sheet. The foldable and second sheets of material are folded around and about the introducer tube and inserted into containment sheath 23. By way of example, containment sheath 23 comprises a 35 cm length of polytetrafluoroethylene material tube with an outside diameter of 0.120" and a wall thickness of approximately 0.010–0.015". The containment sheath has a well-known gas-tight Luer lock connector 36 attached about proximal end 37 thereof. Similarly, proximal end 38 of introducer tube 21 includes a well-known gas-tight Luer lock connector 39 which engages Luer lock connector 36 of the containment sheath and allows passage of wire guide 32 therethrough.

When the repair device is inserted into the peritoneal cavity of a patient and in its unfolded shape 14, the device is positioned over tissue aperture or hernial rings 1–3 with introducer 21 as depicted in FIG. 2. When properly positioned, the unfolded repair device is attached to the tissue surrounding the hernial rings using, for example, well-known suture material or helical coil fasteners 40. In preparation of positioning the repair device over the hernial ring, the physician places two helical coil fasteners opposite each other and centered over the hernial ring at a distance greater than the diameter of the repair device. These two helical coil fasteners serve as markers for the placement of the device. When the repair device is in a satisfactory position with respect to the marker fasteners, suture material or other helical coil fasteners are inserted into the peritoneal cavity via another trocar access sheath and turned through the repair device and into the tissue surrounding the hernial ring using other well-known minimally invasive surgical instruments. When sufficiently attached to surrounding tissue, the containment sheath is brought up against the distal end of the introducer and foldable sheet of material to pull the distal end of the introducer from collar 46 and opening 19 in foldable sheet of material 13. Wire guide 27 is removed from the containment sheath, and the foldable sheet 13 of material and flared distal end 20 of the introducer is pulled against distal end 35 of sheath 23 as depicted in FIG. 6. When the foldable sheet of material is in the unfolded shape with elastic stiffener wire contained in device cavity 18, flared distal end 20 of the introducer is readily pulled out of collar 46 and opening 19 of the folded sheet 13 by engaging the distal end of sheath 23. Alternatively, the repair device is first removed from the distal end of the introducer by engaging the sheath and pulling the introducer out of the device cavity opening. The detached device is then positioned at least partially over the hernial rings and affixed to the surrounding tissue with other surgical instruments passed through other trocar sheaths.

Another procedure for affixing the unfolded repair device to the tissue surrounding the hernial rings is to include an affixation suture loop 41 to second sheet 13 of material, as depicted in FIG. 6. The repair device includes this suture loop which is passed through containment sheath 23. With one affixation technique, the affixation suture loop is passed through the hernial ring and percutaneously drawn through the abdominal wall and skin of the patient. The repair device is positioned at least partially covering the hernial rings, and the affixation suture is pulled and affixed to the surface of the skin using a well-known percutaneous surgical technique. Depending on the position of the tissue apertures or hernial rings, no additional helical coil fasteners or sutures are required for attaching the repair device to the tissue surrounding the apertures. Alternatively, the folded tissue aperture repair device is percutaneously inserted through the tissue aperture or hernial ring and then extended from the containment sheath. The repair device is extended to its unfolded shape, and the introducer and sheath are pulled back through the insertion site with the affixation suture extending from the folded sheet of material and to the surface skin of the patient for affixation thereto.

Figure 8:
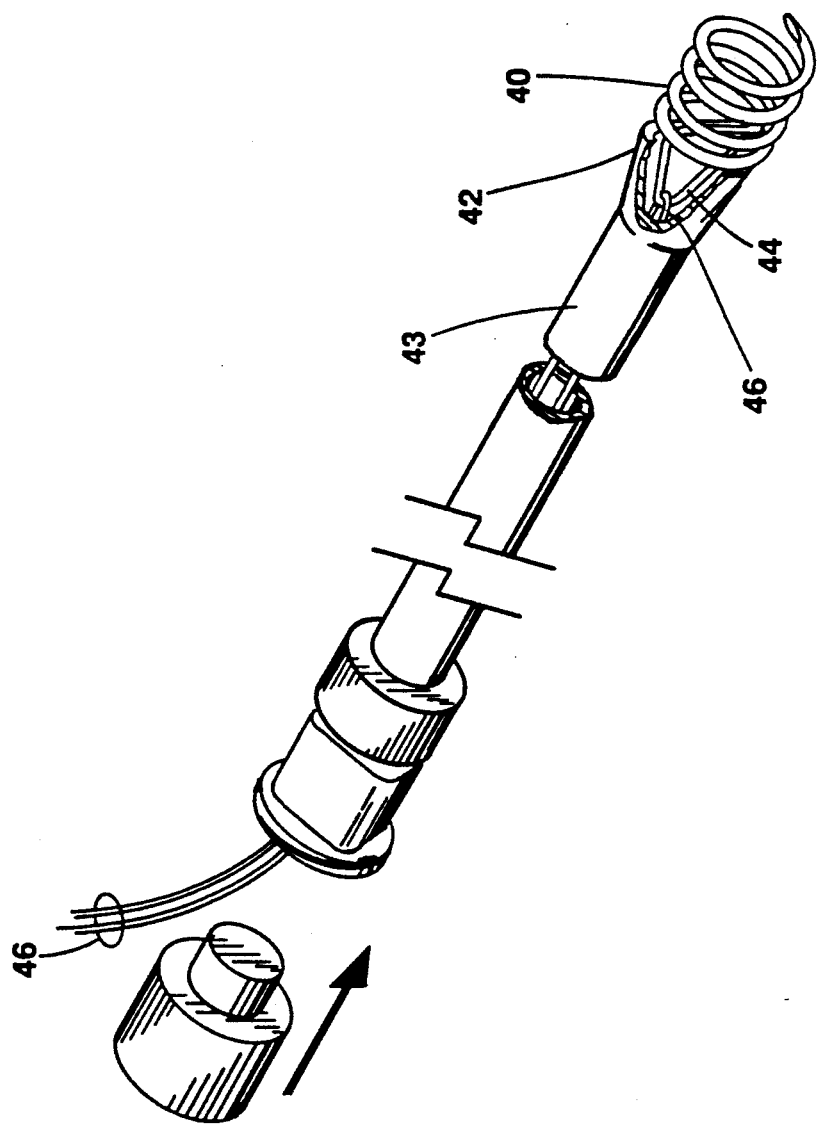
FIG. 8 depicts an illustrative helical coil fastener and application cannula for affixing the repair device of FIG. 3 to tissue surrounding the tissue aperture or hernial ring.

Depicted in FIG. 8 is a helical coil fastener 40 inserted into flared distal end 42 of application cannula 43. By way of example, the helical coil fastener preferably comprises two and a half turns of 0.018" stainless steel wire approximately 0.15" in length with a 0.050–0.060" spacing therebetween. The diameter of the helical coil fastener is approximately 0.125". Eyelet 44 of the fastener extends from the proximal end of the turns and is approximately 0.250" in length. Application cannula 43 comprises a twelve gauge stainless steel cannula having an outside diameter of 0.120" and an inside diameter of approximately 0.095". Flare 42 about the distal end of application cannula includes a major diameter of approximately 0.150" and a minor diameter of approximately 0.065". The application cannula is long enough for insertion through a trocar access sheath. The eyelet is secured in the flared distal end of the application cannula using, for example, a loop 46 of suture material. The helical coil fastener is threaded through the foldable and second sheets of material and into the surrounding tissue with rotation of the application cannula. When secured in tissue, the fastener is released by pulling loop 46 of suture material free of the fastener eyelet and drawing the application cannula from the eyelet.

It is to be understood that the above-described tissue aperture repair device is merely an illustrative embodiment of the principles of this invention and that other tissue aperture repair devices may be devised by those skilled in the art without departing from the spirit and scope of this invention. It is contemplated that the tissue aperture repair device is readily usable in both open surgery and minimally invasive surgical procedures. In open surgery, the repair device includes the elastic stiffener wire already positioned in the device cavity or merely affixed to the circumference of the foldable sheet of material. The elastic stiffener material may also comprise a nickeltitanium alloy such as commercially available nitinol, which possesses a superelastic property to readily maintain the device in its unfolded shape. As a result, the number of turns of the stiffener wire around the circumference of the device can be significantly reduced. Furthermore, the elastic stiffener wire may extend across the diameter of the repair device. Several stiffener wires may be crisscrossed to suit any unfolded shape desired. A crisscrossed configuration is ideally suited for a rectangularly shaped tissue aperture repair device. It is further contemplated that the unfolded shape of the tissue aperture repair device can take on any configuration desired by the physician. Percutaneous insertion of the repair device is contemplated using several different techniques as briefly described above. Furthermore, insertion can be from the patient skin surface through a tissue aperture or hernial ring into the peritoneal cavity. The device is unfolded and drawn against the aperture similar to an extended umbrella. The device may be anchored or sutured to the surrounding tissue or simply fixedly positioned using the affixation suture extending from the foldable sheet. Other techniques for percutaneous positioning include well-known intra-cavity approaches. Furthermore, this tissue aperture repair device is not only suited for peritoneal cavity hernias but for any other tissue aperture occurring anywhere in the body such as the thoracic cavity.

What is claimed is:

1. A tissue aperture repair device comprising:

a foldable sheet of material having an unfolded shape and an unfolded circumference for at least partially covering a tissue aperture; and support means extending and attached circumferentially about said unfolded circumference of said foldable sheet of material for maintaining said foldable sheet of material in said unfolded shape.

2. The tissue aperture repair device of claim 1 wherein said support means comprises stiffener means for applying force to said foldable sheet of material for maintaining said foldable sheet of material in said unfolded shape.

3. The tissue aperture repair device of claim 2 wherein said support means further comprises attachment means for attaching said stiffener means to said foldable sheet of material.

4. The tissue aperture repair device of claim 1 wherein said support means comprises attachment means for attaching said support means to said foldable sheet of material.

5. The tissue aperture repair device of claim 4 wherein said attachment means comprises a second sheet of material attached about said unfolded circumference of said foldable sheet of material and forming a cavity between said foldable and second sheet of material.

6. The tissue aperture repair device of claim 5 wherein said support means further comprises stiffener means for applying force about said unfolded circumference of said foldable sheet of material for maintaining said foldable sheet of material in said unfolded shape and wherein said cavity includes an opening thereto for insertion of said stiffenere means into said cavity.

7. The tissue aperture repair device of claim 6 wherein said stiffener means comprises an elastic wire.

8. The tissue aperture repair device of claim 5 wherein said support means further comprises an elastic wire.

9. The tissue aperture repair device of claim 1 further comprising affixation means for affixing said foldable sheet of material to tissue positioned about said tissue aperture.

10. The tissue aperture repair device of claim 9 wherein said affixation means comprises a length of suture material extending from said foldable sheet of material.

11. The tissue aperture repair device of claim 9 wherein said affixation means comprises a helical fastener insertable through said foldable sheet of material and into said tissue about said tissue aperture.

12. A percutaneously insertable tissue aperture repair device comprising:

a first foldable sheet of material having a first unfolded shape and a first circumference when in said first unfolded shape for at least partially covering a tissue aperture;

a second foldable sheet of material having a second unfolded shape and a second circumference substantially equivalent to said first unfolded shape and said first circumference, respectively, attached about said first circumference of said first foldable sheet of material, and forming a cavity between said first and second foldable sheets of material, at least one of said first and second foldable sheets of material also including an opening positioned therein; and an introducer attached to at least one of said first and second foldable sheets of material foldable thereabout for percutaneous insertion to a tissue aperture and having a hollow passageway extending therein communicating with said cavity through said opening positioned in at least one of said first and second foldable sheets of material.

13. The percutaneously insertable device of claim 12 further comprising a stiffener which when inserted in said cavity maintains at least one of said first and second foldable sheets of material in at least one of said first and second unfolded shapes.

14. The percutaneously insertable device of claim 13 wherein said stiffener comprises an elastic wire.

15. The percutaneously insertable device of claim 14 wherein said elastic wire comprises a nickel-titanium alloy.

16. The percutaneously insertable device of claim 13 further comprising a guide insertable through said passageway of said introducer and having a distal end attached about a proximal end of said stiffener.

17. The percutaneously insertable device of claim 13 further comprising a length of suture material extending from at least one of said first and second foldable sheets of material for percutaneous affixation to tissue about said tissue aperture.

18. The percutaneously insertable device of claim 13 wherein said stiffener has a predetermined length approximately five times at least one of said first and second circumferences of said first and second foldable sheets of material.

19. The percutaneously insertable device of claim 13 wherein an other of said first and second foldable sheets of material comprises a porous material.

20. The percutaneously insertable device of claim 12 further comprising a sheath having a hollow longitudinal passageway therein for containment of at least one of said first and second foldable sheets of material when folded about said introducer.

21. The percutaneously insertable device of claim 12 wherein at least one of said first and second unfolded shapes is elliptical.

22. The percutaneously insertable device of claim 12 wherein at least one of said first and second unfolded shapes is circular.

23. The percutaneously insertable device of claim 12 further comprising a suture material attaching said first and second foldable sheets of material together about said first and second circumferences thereof.

24. The percutaneously insertable device of claim 12 wherein at least one of said first and second foldable sheets of material comprises a prosthetic mesh material 25. A percutaneously insertable hernial ring repair of device comprising:
   a first foldable sheet of material comprising a porous prosthetic mesh positionable against said hernial ring and having an unfolded circular shape and a circumference when in said unfolded circular shape for at least partially covering a hernial ring, said foldable sheet also including an opening centrally positioned therein;
   a second foldable sheet of material comprising a nonporous material positionable facing away from said henial ring and attached about said circumference of said first foldable sheet of material and forming a cavity therebetween;
   a suture positioned about said circumference of said first foldable sheet of material attaching said first and second foldable sheets of material together;
   an introducer positioned through said opening in said first foldable sheet of material and having a hollow passageway extending longitudinally therein and communicating with said cavity, said first and second foldable sheets of material being folded about a distal end of said introducer when positioned in a sheath for percutaneous insertion of said hernial ring;
   a sheath having a hollow passageway extending longitudinally therein and containing said distal end of said introducer with said first and second foldable sheets of material being folded thereabout for percutaneous insertion to said hernial ring;
   an elastic stiffener wire having a predetermined length approximately five times the circumference of said first foldable sheet of material and insertable through said hollow passageway of said introducer and into said cavity for maintenance of said first and second foldable sheets of material in said unfolded circular shape;
   a wire guide having a distal end detachably connected to a proximal end of said elastic stiffener wire for insertion thereof in said cavity; and
   a suture extending from at least one of said first and second foldable sheets of material for attachment thereof to tissue about said hernial ring.

* * * * *